United States Patent [19]

Takeuchi et al.

[11] Patent Number: 5,624,962
[45] Date of Patent: Apr. 29, 1997

[54] AQUEOUS DRUG COMPOSITION HAVING PROPERTY OF REVERSIBLE THERMOSETTING GELATION

[75] Inventors: Masanobu Takeuchi; Hiroe Suzuki; Toshie Takahashi; Hiroki Maruyama; Miyako Fukushima; Keiko Naitou; Touru Oguma; Masayoshi Goto, all of Tokyo, Japan

[73] Assignee: Wakamoto Pharmaceutical Co., Ltd., Tokyo, Japan

[21] Appl. No.: 397,064

[22] PCT Filed: Nov. 10, 1993

[86] PCT No.: PCT/JP93/01636

§ 371 Date: Apr. 12, 1995

§ 102(e) Date: Apr. 12, 1995

[87] PCT Pub. No.: WO94/23750

PCT Pub. Date: Oct. 27, 1994

[30] Foreign Application Priority Data

Apr. 16, 1993 [JP] Japan ................................. 5-112345

[51] Int. Cl.$^6$ ........................... A61K 9/08; A61K 47/36
[52] U.S. Cl. ...................... 514/772.2; 424/78.02
[58] Field of Search ............ 424/78.04, 78.08; 514/772.2

[56] References Cited

U.S. PATENT DOCUMENTS

| | | | |
|---|---|---|---|
| 3,311,577 | 3/1967 | Rankin et al. | 424/78.04 |
| 4,188,373 | 2/1980 | Krezanoski. | |
| 4,474,751 | 10/1984 | Haslam et al.. | |
| 4,474,752 | 10/1984 | Haslam et al.. | |
| 4,474,753 | 10/1984 | Haslam et al.. | |
| 4,478,822 | 10/1984 | Haslam et al.. | |
| 5,077,033 | 12/1991 | Viegas et al. | 424/78.04 |
| 5,252,318 | 10/1993 | Joshi et al. | 424/78.04 |

FOREIGN PATENT DOCUMENTS

| | | |
|---|---|---|
| 2385395 | 10/1978 | France. |
| 62-181228 | 8/1987 | Japan. |
| 2203039 | 10/1988 | United Kingdom. |
| WO91/19481 | 12/1991 | WIPO. |

OTHER PUBLICATIONS

Hakodate technical specialized high school bulletin, No. 22, 113–120 (1987)–Gelation Behaviors of Methylcellulose––Water System in Dynamic Measurement by Mitsuo Ohba.

E. Heymann Trans. Faraday Soc. 31, 846 (1935)—Studies on Sol–Gel Transformations.

Primary Examiner—Peter F. Kulkosky
Attorney, Agent, or Firm—Oblon, Spivak, McClelland, Maier & Neustadt, P.C.

[57] ABSTRACT

An aqueous drug composition having property of reversible thermosetting gelation for ophthalmic, dermatological and body cavitical use which comprises effective amount of drugs used for pharmaceutical therapy or diagnosis, methylcellulose, citric acid and polyethylene glycol and has a pH of 3 to 10, characterized in that said aqueous drug composition is fluid liquid before administration or application and forms gel at a body temperature of a local region immediately after administration or application.

13 Claims, 2 Drawing Sheets

AQUEOUS DRUG COMPOSITION HAVING PROPERTY OF REVERSIBLE THERMOSETTING GELATION

TECHNICAL FIELD

The present invention relates to an aqueous drug composition having property of reversible thermosetting gelation which comprises a pharmacologically effective component, methylcellulose, citric acid and polyethylene glycol (PEG). More specifically, it relates to an aqueous drug composition characterized in that said aqueous drug compositions is fluid liquid at room temperature or lower and, when administered to eyes or body cavities or spread on skin, gelation happens at body temperature of mammal, so as to achieve a greater degree of bioavailability of the pharmacologically effective component and maintain the effect of the drugs for long period.

BACKGROUND ART

Hitherto, many aqueous drug compositions which are liquid at room temperature or lower and form a semi-solid or gel at body temperature of mammal have been disclosed for aqueous drug compositions which effectively release a pharmacologically effective component to mammal to be treated. U.S. Pat. No. 4,188,373 discloses aqueous drug compositions having property of thermosetting gelation, which comprise PLURONIC (trademark) and form gel by heating, and a desired sol-gel transition temperature thereof is obtained by controlling the concentration of PLURONIC. Moreover, U.S. Pat. Nos. 4,474,751, 4,474,752, 4,474,753 and 4,478,822 disclose drug delivery systems utilizing aqueous drug compositions having property of thermosetting gelation. The unique features of these systems are that both the sol-gel transition temperature and/or the rigidity of the gel can be modified by adjustment of the pH and/or the ionic strength and the polymer concentration. More recently, aqueous drug compositions, which form gel at a local region by changing pH and increasing temperature simultaneously (PCT WO 91/19481), are proposed.

However, the safety of the gelling materials used in these aqueous compositions is not necessarily certified with respect to all of the regions to be treated, and the high viscosity of the compositions in liquid state due to the high concentration of polymer in aqueous compositions results in the disadvantage that it cannot be easily used in a certain regions to be treated (for example, eyes). Japanese Patent Application Laid-open 62-181228 discloses a aqueous drug composition having property of sol-gel phase transition by ionic strength. This composition is characterized in that the concentration of the materials giving rise to a sol-gel phase transition is 10–100 times less than that of the aforesaid aqueous drug compositions having property of thermosetting gelation, and that it has no danger of gelation even if the surrounding temperature rises during storage, but it can be applied to only the specific region (for example, eyes).

On the other hand, it is well known that an aqueous solution of methylcellulose forms gel by heating and reverses to sol by cooling, in other words, its sol-gel phase transition is reversible, and researches on its mechanism have been considerably made.

OOba reports the relation of the degree of polymerization of methylcellulose and the concentration of methylcellulose to the gelling temperature, and the modification of gelling temperature by addition of ion, based on the experiment where an aqueous solution of methylcellulose is heated at a fixed rate to form gel (Hakodate technical specialized high school bulletin, No.22, 113–120, 1987). However, there is no description about aqueous compositions comprising methylcellulose which form gel at around body temperature of mammal.

Moreover, E. Heymann has determined the sol-gel transition temperature of an aqueous solution of methylcellulose with the content of methoxyl group of 35.4% (concentration of methylcellulose: 1.6%) when it is combined with salts. However, according to the experiment of the present inventors, when using methylcellulose (content of methoxyl group: 26–33%) as used in the present invention, the aqueous solution of methylcellulose with 0.2 mol of salt concentration (concentration of methylcellulose: 1.6%) has never formed gel at around body temperature of mammal.

DISCLOSURE OF INVENTION

After the present inventors have diligently conducted many researches in order to develop aqueous drug compositions which are liquid at room temperature or lower and form gel at body temperature of mammal by using gelling materials which can be administered to any regions to be treated and whose safeties have been certified, they have found that the excellent aqueous drug compositions which form gel at the temperature of a local region and give no discomfort after administration can be obtained by mixing the appropriate amounts of methylcelullose, citric acid and PEG having a particular range of molecular weight, and completed the present invention.

That is, the present invention relates to an aqueous drug composition having property of reversible thermosetting gelation comprising effective amount of drugs used for pharmaceutical therapy or diagnosis, characterized in that the said composition comprises 0.2 to 2.1 (W/V) % of methylcellulose (the content of methoxyl group is within the range of 26 to 33%), 1.2 to 2.3 (W/V) % of citric acid, 0.5 to 13 (W/V) % of polyethylene glycol and a pharmaceutically acceptable pH adjusting agent in an amount sufficient to adjust pH of composition within the range of 3 to 10. The aqueous drug composition according to the present invention can be easily administered or spread on the region to be treated in a fixed amount since it has good fluidity at room temperature or lower, and moreover, since it forms gel immediately after administration, it can keep a good residence of drugs in any regions and maintain a prolonged effect of drugs.

One of the excellent advantageous features of the composition according to the present invention is that it is liquid with low viscosity at temperature less than body temperature of mammal because of the low concentration of methylcellulose polymer and that it forms semi-solid or gel with very high viscosity immediately after contacted with mammal to be treated. Further, another advantageous feature is that the composition promptly arrives at the region to be treated and shows good contact with the region since it is liquid with low viscosity. Moreover, another advantageous feature is that even if administered to the skin or body cavities of mammal, the pain to be given to the patient can be minimized because it shows no stimulus on eyes.

Any methylcelluloses can be used alone or as a mixture thereof as the methylcellulose (content of methoxyl group: 26–33%) used in the present invention, so long as it has a viscosity of 2% aqueous solution within the range of 13–12, 000 millipascal.sec at 20° C. The content of methoxyl group is preferably within the range of from 26 to 33% in view of the solubility to water. Such methylcelluloses are sold by Shinetsu Chemical Industry Inc. as METOLOSE™ SM 15, SM 25, SM 100, SM 400, SM1500, SM4000, SM 8000 (the number represents the viscosity of 2% aqueous solution at 20° C., millipascal.sec), and by Matsumoto Oil and Fat Pharmaceutical Industry Inc. as MARPOLOSE™ M, and from Dow chemical Co. as METOCEL™A, and all commodities can be easily obtained.

The PEG's used in the present invention are sold by Wako Junyaku Industry Inc. as PEG-200, PEG-300, PEG-600, PEG-1000, PEG-1540, PEG-2,000, PEG-4,000, PEG-6,000, PEG-20,000, PEG-50,000, PEG-500,000, PEG-2,000,000 and PEG-4,000,000, and from Japan Oil and Fat Inc. as MACROGOL-200, MACROGOL-300, MACROGOL-400, MACROGOL-600, MACROGOL-1,500, MACROGOL-1, 540, MACROGOL-4,000, MACROGOL-6,000 and MACROGOL-20,000.

The weight-average molecular weight of the PEG used in the present invention is preferably 300 to 50,000, and particularly 1,000 to 20,000. When the weight-average molecular weight is less than 300, the composition tends to be hard to form gel at a local region, and when it is more than 50,000, the viscosity in liquid state increases and it is not preferred. Two or more kinds of PEG can be mixed to adjust the weight-average molecular weight thereof within the above optimum range.

In the embodiment of the aqueous drug composition having property of reversible thermosetting gelation according to the present invention, the range of the concentration of methylcellulose, citric acid and PEG must be limited for the following reasons.

The concentration of the methylcellulose used in the present invention is within the range of 0.2 to 2.1 (W/v) %. When the concentration of methylcellulose is less than 0.2 (W/V) %, the composition becomes hard to form gel at a local region and, when the concentration is more than 2.1 (W/V) %, the sol shows unduly high viscosity which results in incorrect dosage and it is not preferred.

The concentration of the citric acid is within the range of 1.2 to 2.3 (W/V) %. When the concentration of citric acid is less than 1.2 (w/v) %, the composition becomes hard to form gel at a local region and, when the concentration is more than 2.3 (w/V) %, it is not preferred in view of the stimulus on eyes.

The concentration of the PEG is within the range of 0.5–13 (W/V) %. When the concentration of PEG is less than 0.5 (W/V) %, the composition becomes hard to form gel at a local region and hence loses practical value and, when the concentration is more than 13 (W/V) %, the sol shows high viscosity and it is not preferred.

Furthermore, the gelling temperature of the composition is preferably from about 20° C. to about 40° C. since it is desired that the composition is liquid at room temperature or lower and forms gel at body temperature of mammal.

The aqueous drug composition of the present invention may be used for the therapy and diagnosis of diseases of, for example, eyes, skin and body cavities. The examples of medicines and diagnostics which can be comprised in the composition of the present invention and administered to eyes of mammal, are as follows: chemotherapeutics such as amphotericin B, norfloxacin, miconazole nitrate, ofloxacin and idoxuridine; antibiotics preparation such as chloramphenicol, colistin sodium methanesulfonate, carbenicillin sodium and gentamicin sulfate; antiallergic agents such as 3'-(1H-tetrazol-5-yl)oxanilic acid(MTCC), ketotifen fumarate and sodium cromoglicate; anti-inflammatory agents such as betamethasone sodium phosphate, dexamethasone, fluorometholone, glycyrrhizinate dipotassium, lysozyme chloride, diclofenac sodium, pranoprofen, indomethacin, cortisone acetate, azulene, allantoin and $\epsilon$-aminocaproic acid; miotics and preparations such as pilocarpine hydrochloride and carbachol; vitamin preparations such as flavin adenine dinucleotide, pyridoxal phosphate and cyanocobalamin; vasoconstrictors such as naphazoline nitrate and phenylephrine hydrochloride; antihistamines such as chlorpheniramine maleate and diphenhydramine hydrochloride; mydriatics and preparations such as tropicamide; antiglaucoma drugs such as timolol maleate and carteolol hydrochloride; anticataract drugs such as glutathione and pirenoxine; local anesthetics such as lidocaine hydrochloride and oxybuprocaine hydrochloride; ophthalmic diagnostic agents such as fluorescein sodium; immunosuppressive agents such as ciclosporin and azathioprine; antimetabolic agents such as fluorouracil and tegafur; decongestants such as epinephrine hydrochloride; anti diabetic retinopathy agent such as [5-(3-thienyl)tetrazol-1-yl]acetic acid(TAT); amino acids such as chondroitin sulfate sodium and aminoethylsulfonic acid; autonomic nerve agents such as neostigmine methylsulfate, and mixtures thereof; and other drugs may be used for the theraphy of the symptom and focus of eyes.

The examples of drugs which can be comprised in the composition of the present invention and administered to skin of mammal, are as follows: anti-dermoinfectives such as bifonazole, siccanin, bisdequalinium acetate, clotrimazole and salicylic acid; dermatics for purulence such as sulfamethoxazole sodium, erythromycin and gentamicin sulfate; analgesics and anti-inflammatory agents such as indomethacin, ketoprofen, betamethasone valerate and fluocinolone acetonide; anti-itchings such as diphenhydramine; local anesthetics such as procaine hydrochloride and lidocaine hydrochloride; antimicrobials for dermatologic use such as iodine, povidone iodine, benzalkonium chloride and chlorhexidine gluconate.

The examples of drugs which can be comprised in the composition of the present invention and administered to body cavities of mammal, that is, rectum, urethra, nasal cavity, vagina, auditory meatus, oral cavity and buccal pouch, are as follows: antihistamines such as diphenhydramine hydrochloride and chlorpheniramine maleate; agents affecting genital organs such as clotrimazole, naphazoline nitrate, ketotifen fumarate and miconazole nitrate; agents for otic and nosal use such as tetryzoline hydrochloride; bronchodilators such as aminophylline; antimetabolic agents such as fluorouracil; hypnotics and sedatives such as diazepam; antipyretics,analgesics and anti-inflammatory agents such as aspirin, indomethacin, sulindac, phenylbutazone and ibuprofen; adrenal hormone preparations such as dexamethasone, triamcinolone and hydrocortisone; local anesthetics such as lidocaine hydrochloride; dermatics for purulence such as sulfisoxazole, kanamycin, tobramycin and erythromycin; synthetic antibacterials such as norfloxacin and nalidixic acid.

Generally, the composition preferably contains from about 0.001% to about 10% by weight of the effective drug, though it may vary depending on the type of the drug.

The examples of the pH adjusting agents used in the composition of the present invention include acids such as hydrochloric acid, sulfuric acid, boric acid, phosphoric acid and acetic acid and bases such as sodium hydroxide, monoethanolamine, diethanolamine and triethanolamine.

If necessary, the aqueous drug composition of the present invention may contain pharmaceutically acceptable buffering agents, salts, preservatives and solubilizing agents and the like. The examples of the preservatives may include invert soaps such as benzalkonium chloride, benzethonium chloride and chlorhexyzine gluconate, parabens such as methylparaben, ethylparaben, propylparaben and butylparaben, alcohols such as chlorobutanol, phenylethylalcohol and benzyl alcohol, organic acids and salts thereof such as dehydro sodium acetate, sorbic acid and sodium sorbate. Moreover, surfactants or chelating agents may be suitably added to the composition. Generally, these components may be used within the range of about 0.001 to 2% by weight, and preferably within the range of about 0.002 to 1% by weight. The examples of buffering agents include alkaline metal salts of acids such as phosphoric acid, boric acid, acetic acid, tartaric acid, lactic acid and carbonic acid, amino acids such as glutamic acid, ε-aminocaproic acid, aspartic acid, glycine, arginine and lysine, and taurine, tris (hydoroxymethyl) aminomethane. These buffering agents may be added to the composition in a sufficient amount to maintain pH within the range of 3 to 10.

The examples of the solubilizing agents include POLYSORBATE80, polyoxyethylene hydrogenated castor oil and cyclodextrin and they may be used within a range of 0 to 15% by weight.

The process of preparing the aqueous drug composition of the present invention is not particularly restricted and, for example, comprises dissolving citrate and PEG in sterilized water, adjusting the pH of this solution with a pH adjusting agent, adding drugs and necessary preservatives, adding a solution where methylcellulose is dissolved in sterilized water, adjusting pH again, filling up the volume of the mixture with sterilized water and stirring the composition with cooling. If necessary, after this procedure, a variety of additive, for example, buffering agents, salts and preservatives, may be added. Moreover, if drugs are slightly soluble or insoluble, they may be suspended or solubilized by solubilizing agents before use.

BEST MODE FOR CARRYING OUT THE INVENTION

Figure 1:
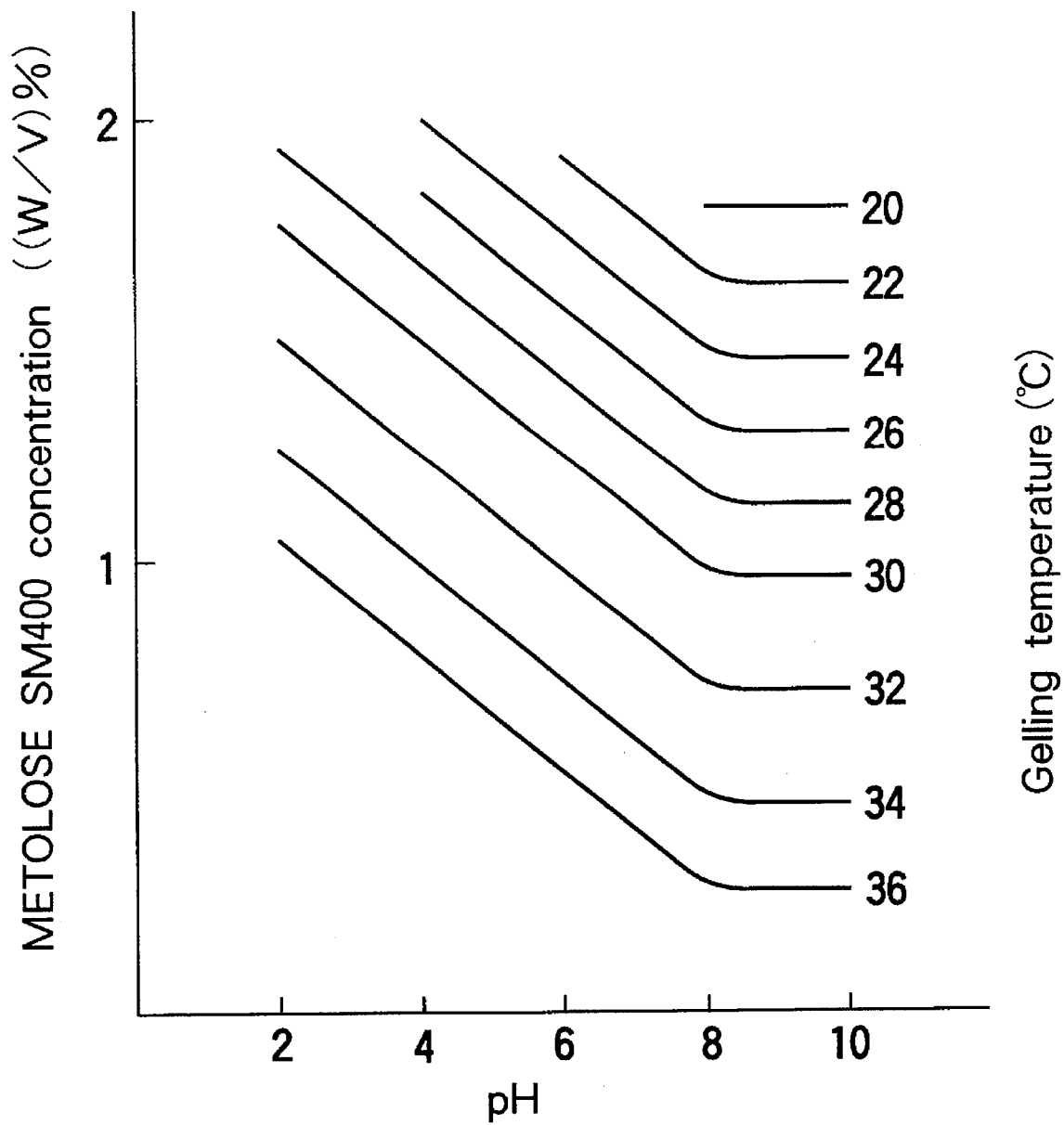
FIG. 1 shows the relation of METOLOSE concentration and pH in the aqueous composition to gelling temperature. The axis of ordinate represents the concentration of METOLOSE SM 400 ((W/V)%) and the axis of abscissa represents pH.

The following examples are provided to illustrate a variety of embodiment of the present invention and are not intended to limit the range of the present invention.

EXAMPLES

Example 1

2.3 g of citric acid, 6.0 g of POLYETHYLENE GRYCOL 4000 (weight-average molecular weight is 3000, available from Wako Junyaku Industry Inc.), 0.5 g of chlorobutanol are dissolved in 50 ml of sterilized water. To this added are 0.1 g of idoxuridine dissolved in 10 ml of 3N sodium hydroxide and 0.5 g of METOLOSE SM 400 (available from Shinetsu Chemical Industry Inc.) dissolved in 25 ml of sterilized water. Then, pH is adjusted to 6.0 with 3N sodium hydroxide and the volume of the mixture is filled up to 100 ml with sterilized water, and the components are dissolved by stirring well with ice cooling to give eye drops.

Example 2

2.3 g of citric acid, 6.0 g of POLYETHYLENE GRYCOL 4000 are dissolved in 50 ml of sterilized water and pH is adjusted to 5.0 with 3N sodium hydroxide. To this added are 0.3 g of norfloxacin, 0.005 g of benzalkonium chloride and, furthermore, 0.5 g of METOLOSE SM 400 dissolved in 25 ml of sterilized water. Then, pH is adjusted to 5.5 with 3N sodium hydroxide and the volume of the mixture is filled up to 100 ml with sterilized water, and the components are dissolved by stirring well with ice cooling to give eye drops.

Examples 3–6

By a method similar to that of Example 2, eye drops of which compositions are shown in Table 1, are prepared.

Example 7

0.026 g of methylparaben and 0.014 g of propylparaben are added to 50 ml of sterilized water prewarmed to about 60° C. and are well stirred to be dissolved. After this solution is cooled to room temperature, 2.3 g of citric acid, 6.0 g of POLYETHYLENE GRYCOL 4000 and 0.25 g of chlorobutanol are added to this and dissolved, then pH is adjusted to 5.0 with monoethanolamine. To this mixture, 0.1 g of MTCC is added and, furthermore, 0.5 g of METOLOSE SM 400 dissolved in 25 ml of sterilized water is added. Then pH is adjusted to 5.5 with monoethanolamine and the volume of the mixture is filled up to 100 ml by sterilized water and the components are dissolved by stirring well with ice cooling to give eye drops.

Example 8

By a method similar to that of Example 7, eye drops of which compositions are shown in Table 1, are prepared.

Example 9

0.1 g of pranoprofen, 2.3 g of citric acid and 6.0 g of POLYETHYLENE GRYCOL 4000 are added to 50 ml of sterilized water and stirred well, then pH is adjusted to 6.5 with monoethanolamine. To this added is 0.005 g of benzalkonium chloride and, furthermore, 0.5 g of METOLOSE SM 400 dissolved in 25 ml of sterilized water. Then pH is adjusted to 7.4 with monoethanolamine and the volume of the mixture is filled up to 100 ml by sterilized water, and the components are dissolved by stirring well with ice cooling to give eye drops.

Example 10

0.026 g of methylparaben and 0.014 g of propylparaben are added to 50 ml of sterilized water prewarmed to about 60° C. and are stirred well to be dissolved. After this solution is cooled to room temperature, 0.05 g of naphazoline nitrate, 3.5 g of sodium citrate dihydrate and 6.0 g of POLYETHYLENE GRYCOL 4000 are added to the solution and dissolved. To this mixture, 0.5 g of METOLOSE SM 400 dissolved in 25 ml of sterilized water is added and stirred well. Then pH is adjusted to 5.8 with 1N hydrochloric acid and the volume of the mixture is filled up to 100 ml by sterilized water, and the components are dissolved by stirring well with ice cooling to give eye drops.

Examples 11–13

By a method similar to that of Example 10, eye drops of which compositions are shown in Table 1, are prepared.

Example 14

0.34 g of timolol maleate, 3.5 g of sodium citrate dihydrate, 6.0 g of POLYETHYLENE GRYCOL 4000 and 0.005 g of benzalkonium chloride are added to 50 ml of sterilized water and dissolved. To this, 0.5 g of METOLOSE SM 400 dissolved in 25 ml of sterilized water is added and stirred well. Then, pH is adjusted to 6.8 with 1N hydrochloric acid or 1N sodium hydroxide and the volume of the mixture is filled up to 100 ml with sterilized water and the components are dissolved by stirring well with ice cooling to give eye drops.

Examples 15–19

By a method similar to that of Example 14, eye drops of which compositions are shown in Table 1, are prepared.

Examples 20–22

By a method similar to that of Example 14, agents for dermal use of which compositions are shown in Table 1, are prepared.

Example 23

By a method similar to that of Example 10, agents for dermal use of which compositions are shown in Table 1, are prepared.

Example 24–31

By a method similar to that of Example 14, agents for body cavitical use of which compositions are shown in Table 1, are prepared.

TABLE 1

| Example | Component | W/V % | Gelling temp. |
|---|---|---|---|
| 1 | Idoxuridine | 0.1 | 36 |
|  | SM 400 | 0.5 |  |
|  | Citric acid | 2.3 |  |
|  | PEG 4000 | 6.0 |  |
|  | Chlorobutanol | 0.5 |  |
|  | 3N NaOH | to pH 6.0 |  |
| 2 | Norfloxacin | 0.3 | 36 |
|  | SM 400 | 0.5 |  |
|  | Citric acid | 2.3 |  |
|  | PEG 4000 | 6.0 |  |
|  | Benzalkonium chloride | 0.005 |  |
|  | 3N NaOH | to pH 5.5 |  |
| 3 | Gentamicin sulfate | 0.3 g titer | 36 |
|  | SM 400 | 0.5 |  |
|  | Citric acid | 2.3 |  |
|  | PEG 4000 | 6.0 |  |
|  | Benzalkonium chloride | 0.005 |  |
|  | 3N NaOH | to pH 7.0 |  |
| 4 | Sodium cromoglicate | 2.0 | 36 |
|  | SM 400 | 0.5 |  |
|  | Citric acid | 2.3 |  |
|  | PEG 4000 | 6.0 |  |
|  | Benzalkonium chloride | 0.01 |  |
|  | 3N NaOH | to pH 6.5 |  |
| 5 | Betamethasone sodium phosphate | 0.1 | 34 |
|  | SM 400 | 0.5 |  |
|  | Citric acid | 2.3 |  |
|  | PEG 4000 | 6.0 |  |
|  | Benzalkonium chloride | 0.01 |  |
|  | POLYSORBATE 80 | 0.2 |  |
|  | 3N KOH | to pH 8.2 |  |

TABLE 1-continued

| Example | Component | W/V % | Gelling temp. |
|---|---|---|---|
| 6 | Lidocaine hydrochloride | 0.5 | 36 |
|  | SM 400 | 0.5 |  |
|  | Citric acid | 2.3 |  |
|  | PEG 4000 | 6.0 |  |
|  | Benzalkonium chloride | 0.005 |  |
|  | Triethanolamine | to pH 6.5 |  |
| 7 | MTCC | 0.1 | 36 |
|  | SM 400 | 0.5 |  |
|  | Citric acid | 2.3 |  |
|  | PEG 4000 | 6.0 |  |
|  | Methylparaben | 0.026 |  |
|  | Propylparaben | 0.014 |  |
|  | Chlorobutanol | 0.25 |  |
|  | Monoethanolamine | to pH 5.5 |  |
| 8 | Flavin adenine dinucleotide | 0.05 | 36 |
|  | SM 400 | 0.5 |  |
|  | Citric acid | 2.3 |  |
|  | PEG 4000 | 6.0 |  |
|  | Methylparaben | 0.026 |  |
|  | Propylparaben | 0.014 |  |
|  | Diethanolamine | to pH 6.7 |  |
| 9 | Pranoprofen | 0.1 | 34 |
|  | SM 400 | 0.5 |  |
|  | Citric acid | 2.3 |  |
|  | PEG 4000 | 6.0 |  |
|  | Benzalkonium chloride | 0.005 |  |
|  | Monoethanolamine | to pH 7.4 |  |
| 10 | Naphazoline nitrate | 0.05 | 36 |
|  | SM 400 | 0.5 |  |
|  | Sodium citrate dihydrate | 3.5 |  |
|  | PEG 4000 | 6.0 |  |
|  | Methylparaben | 0.026 |  |
|  | Propylparaben | 0.014 |  |
|  | 1N HCl | to pH 5.8 |  |
| 11 | Pilocarpine hydrochloride | 0.5 | 36 |
|  | SM 400 | 0.5 |  |
|  | Sodium citrate dihydrate | 3.5 |  |
|  | PEG 4000 | 6.0 |  |
|  | Methylparaben | 0.026 |  |
|  | Propylparaben | 0.014 |  |
|  | Chlorobutanol | 0.25 |  |
|  | 1N HCl | to pH 5.2 |  |
| 12 | Pirenoxine | 0.005 | 36 |
|  | SM 400 | 0.5 |  |
|  | Sodium citrate dihydrate | 3.5 |  |
|  | PEG 4000 | 9.0 |  |
|  | Methylparaben | 0.026 |  |
|  | Propylparaben | 0.014 |  |
|  | 1N HCl | to pH 6.0 |  |
| 13 | TAT | 2.2 | 36 |
|  | SM 400 | 0.5 |  |
|  | Sodium citrate dihydrate | 3.5 |  |
|  | PEG 4000 | 6.0 |  |
|  | Methylparaben | 0.026 |  |
|  | Propylparaben | 0.014 |  |
|  | POLYSORBATE 80 | 0.005 |  |
|  | 1N NaOH | to pH 5.5 |  |
| 14 | Timolol maleate | 0.34 | 36 |
|  | SM 400 | 0.5 |  |
|  | Sodium citrate dihydrate | 3.5 |  |
|  | PEG 4000 | 6.0 |  |
|  | Benzalkonium chloride | 0.005 |  |
|  | 1N HCl or 1N NaOH | to pH 6.8 |  |
| 15 | Timolol maleate | 0.34 | 32 |
|  | SM 400 | 0.7 |  |
|  | SM 15 | 0.7 |  |
|  | Sodium citrate dihydrate | 3.5 |  |
|  | PEG 4000 | 2.0 |  |
|  | Benzalkonium chloride | 0.005 |  |
|  | 1N HCl or 1N NaOH | to pH 6.8 |  |
| 16 | Ciclosporin | 0.05 | 36 |
|  | SM 400 | 0.5 |  |
|  | Sodium citrate dihydrate | 3.5 |  |
|  | PEG 4000 | 6.0 |  |
|  | Benzalkonium chloride | 0.005 |  |
|  | 1N HCl | to pH 6.0 |  |

TABLE 1-continued

| Example | Component | W/V % | Gelling temp. |
|---|---|---|---|
| 17 | Fluorouracil | 1.0 | 34 |
| | SM 400 | 0.5 | |
| | Sodium citrate dihydrate | 3.5 | |
| | PEG 4000 | 6.0 | |
| | Benzalkonium chloride | 0.005 | |
| | 1N NaOH | to pH 8.4 | |
| 18 | Fluorescein sodium | 1.0 | 34 |
| | SM 15 | 2.1 | |
| | Sodium citrate dihydrate | 3.5 | |
| | PEG 20000 | 1.0 | |
| | 1N HCl or 1N NaOH | to pH 7.4 | |
| 19 | Tropicamide | 0.5 | 36 |
| | Phenylephrine hydrochloride | 0.5 | |
| | SM 400 | 0.5 | |
| | Sodium citrate dihydrate | 3.5 | |
| | PEG 4000 | 6.0 | |
| | Benzalkonium chloride | 0.005 | |
| | 1N HCl | to pH 5.5 | |
| 20 | Clotrimazole | 1.0 | 26 |
| | SM 1500 | 2.1 | |
| | Sodium citrate dihydrate | 1.8 | |
| | PEG 4000 | 5.0 | |
| | Benzalkonium chloride | 0.01 | |
| | 1N HCl or 1N NaOH | to pH 7.0 | |
| 21 | Diphenhydramine hydrochloride | 1.0 | 28 |
| | SM 1500 | 2.1 | |
| | Sodium citrate dihydrate | 1.8 | |
| | PEG 4000 | 5.0 | |
| | Benzalkonium chloride | 0.01 | |
| | 1N HCl | to pH 5.5 | |
| 22 | Povidone iodine | 5.0 | 32 |
| | SM 1500 | 2.1 | |
| | Sodium citratedihydrate | 1.8 | |
| | PEG 4000 | 5.0 | |
| | 1N HCl | to pH 3.0 | |
| 23 | Indomethacin | 1.0 | 26 |
| | SM 1500 | 2.1 | |
| | Sodium citrate dihydrate | 1.8 | |
| | PEG 4000 | 5.0 | |
| | Methylparaben | 0.1 | |
| | 1N HCl or 1N NaOH | to pH 7.0 | |
| 24 | Miconazole nitrate | 1.0 | 28 |
| | SM 1500 | 2.1 | |
| | Sodium citrate dihydrate | 1.8 | |
| | PEG 4000 | 5.0 | |
| | 1N HCl | to pH 5.5 | |
| 25 | Tetryzoline hydrochloride | 0.1 | 26 |
| | SM 1500 | 2.1 | |
| | Sodium citrate dihydrate | 1.8 | |
| | PEG 4000 | 5.0 | |
| | Benzalkonium chloride | 0.005 | |
| | 1N HCl | to pH 6.5 | |
| 26 | Tetryzoline hydrochloride | 0.1 | 36 |
| | SM 8000 | 1.0 | |
| | Sodium citrate dihydrate | 1.8 | |
| | PEG 4000 | 5.0 | |
| | Benzalkonium chloride | 0.005 | |
| | 1N HCl | to pH 6.5 | |
| 27 | Tetryzoline hydrochloride | 0.1 | 22 |
| | SM 1500 | 2.1 | |
| | Sodium citrate dihydrate | 1.8 | |
| | PEG 4000 | 13.0 | |
| | Benzalkonium chloride | 0.005 | |
| | 1N HCl | to pH 6.5 | |
| 28 | Aminophylline | 2.5 | 26 |
| | SM 1500 | 2.1 | |
| | Sodium citrate dihydrate | 1.8 | |
| | PEG 4000 | 5.0 | |
| | Benzalkonium chloride | 0.005 | |
| | 1N NaOH | to pH 9.0 | |
| 29 | Diazepam | 0.5 | 26 |
| | SM 1500 | 2.1 | |
| | Sodium citrate dihydrate | 1.8 | |
| | PEG 4000 | 5.0 | |
| | Benzalkonium chloride | 0.005 | |
| | 1N HCl | to pH 6.5 | |
| 30 | Dexamethasone | 0.1 | 26 |
| | SM 1500 | 2.1 | |
| | Sodium citrate dihydrate | 1.8 | |
| | PEG 4000 | 5.0 | |
| | Benzalkonium chloride | 0.005 | |
| | 1N HCl | to pH 5.5 | |
| 31 | Erythromycin | 0.1 | 28 |
| | SM 1500 | 2.1 | |
| | Sodium citrate dihydrate | 1.8 | |
| | PEG 4000 | 5.0 | |
| | Benzalkonium chloride | 0.005 | |
| | 1N HCl or 1N NaOH | to pH 7.0 | |

Test Example 1 (Concentration of METOLOSE, pH and gelling temperature)

3.5 g of sodium citrate dihydrate and 6.0 g of POLYETHYLENE GRYCOL 4000 were dissolved in 50 ml of sterilized water, then, 0.3 to 2. 0 g of METOLOSE SM 400 dissolved in 25 ml of sterilized water was added to the solution and pH was adjusted to 3.0 to 10.0 with 3N HCl or 3N NaOH, the volume of the mixture was filled up to 100 ml by sterilized water and the components were dissolved by stirring well with ice cooling to prepare an aqueous composition. The gelling temperature was determined for each aqueous composition. The results obtained are shown in FIG. 1.

Test Example 2 (Test of feeling when applied to human)

1.9 to 2.9 g of citric acid and 4.2 g of POLYETHYLENE GRYCOL 4000 were dissolved in 50 ml of sterilized water, then pH was adjusted to 6.8 with 3N NaOH, the volume of the mixture was filled up to 100 ml with sterilized water and the components were dissolved by stirring well with ice cooling to prepare the aqueous compositions 1 to 4. Further, 1.9 to 2.9 g of citric acid and 4.2 g of POLYETHYLENE GRYCOL 4000 are dissolved in 50 ml of sterilized water, pH is adjusted to 6.0 with diethanolamine. To this added was 0.7 g of METOLOSE SM 400 dissolved in 25 ml of sterilized water and then, pH was adjusted to 6.8 with diethanolamine and the volume of the mixture was filled up to 100 ml with sterilized water and the components were dissolved by stirring well with ice cooling to prepare the aqueous compositions 5 to 8.

As to the stimulus on eyes, the sensory test was carried out in the panel of twenty persons. The standard of evaluation are as follows: "−" represents "non-stimulus", "+" represents "slight smart" and "++" represents "smart". The results of this test are shown in Tables 2 and 3.

TABLE 2

| Aqueous composition | Methylcellulose SM-400 conc. (W/V) % | PEG 4000 conc. (W/V) % | Citric acid conc.[1] (W/V) % | Stimulus on eyes |
|---|---|---|---|---|
| Composition 1 | 0.7 | 4.2 | 1.9 | − |
| Composition 2 | 0.7 | 4.2 | 2.3 | − |
| Composition 3 | 0.7 | 4.2 | 2.5 | + |
| Composition 4 | 0.7 | 4.2 | 2.9 | ++ |

[1]Sodium hydroxide was used as a pH adjusting agent.

TABLE 3

| Aqueous composition | Methyl-cellulose SM-400 conc. (W/V) % | PEG 4000 conc. (W/V) % | Citric acid conc.[1] (W/V) % | Stimulus on eyes |
| --- | --- | --- | --- | --- |
| Composition 5 | 0.7 | 4.2 | 1.9 | − |
| Composition 6 | 0.7 | 4.2 | 2.3 | − |
| Composition 7 | 0.7 | 4.2 | 2.5 | + |
| Composition 8 | 0.7 | 4.2 | 2.9 | ++ |

[1] Diethanolamine was used as a pH adjusting agent.

As clearly shown by the results of Tables 2 and 3, the concentration of citric acid more than 2.5 (W/V) % gave stimulus on eyes regardless of the kind of citrate. As opposed to that, the aqueous compositions of the present invention gave no stimulus on eyes.

Test Example 3 (Test to examine the transition of timolol to albino rabbit aqueous humor)

In the method of Example 14, methylcellulose, sodium citrate and PEG were replaced by 0.9 g of sodium chloride to prepare Composition 9. Moreover, in the method of Example 14, PEG was omitted to prepare Composition 10. The transition of timolol comprised in the composition of Example 14 and Compositions 9, 10 to aqueous humor, was determined in eyes of male albino rabbits (body weight: 2.5–3.5 kg), of which 1 group was consisted of 6 eyes. 50 µl of the eye drops was instilled to the albino rabbit eyes and the concentration of timolol in aqueous humor was determined at 10 minutes, 30 minutes, 1 hour, 2 hours, 4 hours after the administration. The results of this test are shown in Table 4.

TABLE 4

| | Concentration of timolol in aqueous humor(µg/ml) | | | | |
| --- | --- | --- | --- | --- | --- |
| | 10 minutes | 30 minutes | 1 hour | 2 hours | 4 hours |
| Ex. 14 | 1.2 ± 0.5 | 3.4 ± 0.9 | 3.0 ± 0.2 | 1.4 ± 0.3 | 0.2 ± 0.2 |
| Com. 9 | 0.5 ± 0.3 | 0.9 ± 0.4 | 0.9 ± 0.3 | 0.4 ± 0.1 | 0.1 ± 0.1 |
| Com. 10 | 0.7 ± 0.4 | 1.3 ± 0.3 | 0.9 ± 0.1 | 0.5 ± 0.0 | 0.1 ± 0.1 |

As clearly shown by the results of Table 4, the aqueous composition of the present invention maintained high concentration for longer period than the eye drops which do not form gel in a local region.

Test Example 4 (Test to examine the transition of timolol to albino rabbit blood)

The transition of timolol comprised in the composition of Example 9 and Composition 9, was determined in albino rabbits (body weight: 2.5–3.5 kg) of which 1 group consisted of 5 to 6 rabbits. 50 µl of the eye drops was instilled to the albino rabbit eyes and the concentration of timolol in blood was determined at 10 minutes, 30 minutes, 1 hour, 2 hours, 4 hours and 6 hours after the administration. The results of this test are shown in FIG. 2.

Figure 2:
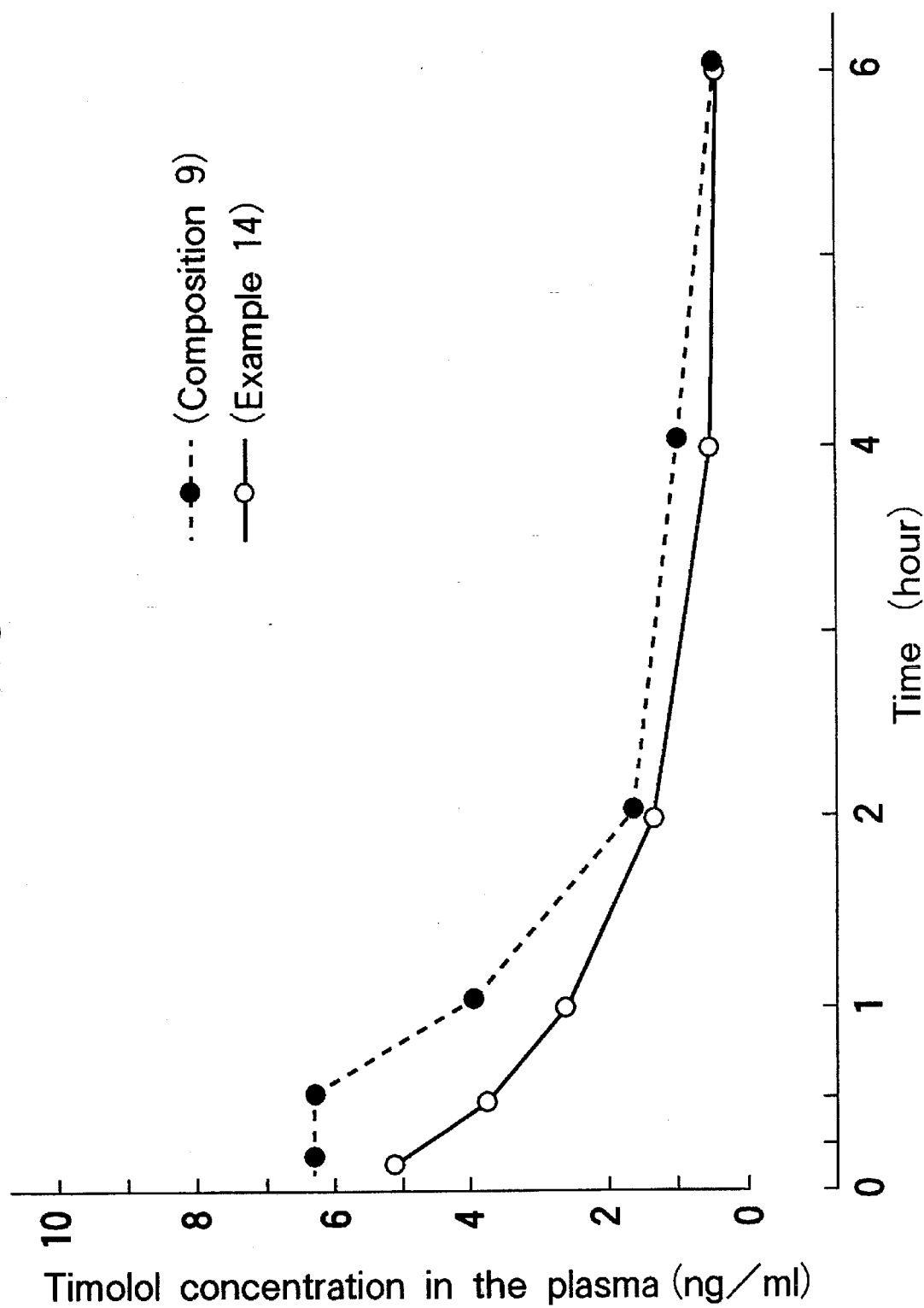
FIG. 2 shows the time course of timolol concentration in the plasma of the albino rabbit following the topical instillation of the aqueous composition. The axis of ordinate represents the concentration of timolol (ng/ml) and the axis of abscissa represents time (hour).

As clearly shown by the results of FIG. 2, the aqueous composition of the present invention represses the transition of timolol to blood and may decrease the systemic side effects in compare with the eye drops which do not form gel in a local region.

We claim:

1. An aqueous drug composition having a property of reversible thermosetting gelation, comprising an effective amount of one or more drugs used in pharmaceutical therapy or diagnosis, wherein the composition comprises 0.2 to 2.1 (W/V) % of methylcellulose having a content of methoxyl group within the range of 26 to 33%; 1.2 to 2.3 (W/V) % of citric acid, 0.5 to 13 (W/V) % of polyethylene glycol and a pharmaceutically acceptable pH adjusting agent in an amount sufficient to adjust the pH of the composition within a range of 3 to 10; and wherein said polyethylene glycol has a weight-average molecular weight of 300 to 50,000.

2. The aqueous drug composition according to claim 1, suitable for ophthalmic use, wherein the pharmaceutically effective drug is selected from the group consisting of chemotherapeutics, antibiotics preparation, antiallergic agents, anti-inflammatory agents, miotics and preparations, vitamin preparations, vasoconstrictors, antihistamines, mydriatics and preparations, antiglaucoma drugs, anticataract drugs, local anesthetics, ophthalmic diagnostic agents, immunosuppressive agents, antimetabolic agents, decongestants, autonomic nerve agents, anti diabetic retinopathy agent, amino acids and mixtures thereof.

3. The composition according to claim 2, wherein the drug is selected from the group of compounds consisting of amphotericin B, norfloxacin, miconazole nitrate, ofloxacin, idoxuridine, chloramphenicol, colistin sodium methanesulfonate, carbenicillin sodium, gentamicin sulfate, ketotifen fumarate, sodium cromoglicate, 3-(1H-tetrazole-5-yl) oxanilic acid, betamethasone sodium phosphate, dexamethasone, fluorometholone, glycyrrhizinate dipotassium, lysozyme chloride, diclofenac sodium, pranoprofen, indomethacin, cortisone acetate, azulene, allantoin, ε-aminocaproic acid, pilocarpine hydrochloride, carbachol, flavin adenine dinucleotide, pyridoxal phosphate, cyanocobalamin, naphazoline nitrate, phenylephrine hydrochloride, chlorpheniramine maleate, diphenhydramine hydrochloride, tropicamide, timolol maleate, carteolol hydrochloride, glutathione, pirenoxine, oxybuprocaine hydrochloride, lidocaine hydrochloride, fluorescein sodium, ciclosporin, azathioprine, fluorouracil, tegafur, epinephrine hydrochloride, neostigmine methylsulfate, [5-(3-thienyl)tetrazol-1-yl]acetic acid and chondroitin sulfate sodium.

4. The composition according to claim 2, wherein the chemotherapeutics is idoxuridine or norfloxacin, the antibiotics preparation is gentamicin sulfate, the antiallergic agent is 3-(1H-tetrazol-5-yl)oxanilic acid or sodium cromoglicate, the anti-inflammatory agent is betamethasone sodium phosphate or pranoprofen, the vitamin preparation is flavin adenine dinucleotide, the local anesthetics is lidocaine hydrochloride, the vasoconstrictors is naphazoline nitrate, the miotics and preparation is pilocarpine hydrochloride, the antiglaucoma drug is timolol maleate, the anticataract drug is pirenoxine, the immunosuppressive agent is ciclosporin, the antimetabolic agent is fluorouracil, the ophthalmic diagnostic agent is fluorescein sodium, the mydriatics and preparation is tropicamide and the anti diabetic retinopathy agent is [5-(3-thienyl)tetrazol-1-yl ]acetic acid.

5. The aqueous drug composition according to claim 1, suitable for local or dermatological use, wherein the pharmaceutically effective drug is selected from the group consisting of anti-dermoinfectives, dermatics for purulence, analgesics and anti-inflammatory agents, anti-itchings, local anesthetics and antimicrobials for dermatologic use.

6. The composition according to claim 5, wherein the drug is selected from the compounds consisting of clotrimazole, salicylic acid, bifonazole, siccanin, bisdequalinium acetate, sulfamethoxazol sodium, erythromycin, gentamicin sulfate, indomethacin, ketoprofen, diphenhydramine, procaine hydrochloride, lidocaine hydrochloride, iodine, povidone iodine, benzalkonium chloride, chlorhexidine gluconate, betamethasone valerate and fluocinolone acetonide.

7. The composition according to claim 5, wherein the anti-dermoinfectives is clotrimazole, the dermatics for purulence is gentamicin sulfate, the analgesics and anti-inflammatory agent is indomethacin, the anti-itchings is diphenhydramine, the local anesthetics is lidocaine hydrochloride and the antimicrobials for dermatologic use is povidone iodine.

8. The aqueous drug composition according to claim 1 therefore, suitable for administration into body cavities wherein the pharmaceutically effective drug is selected from the group consisting of antihistamines, agents affecting genital organs, agents for otic and nasal use, bronchodilators, antimetabolic agents, hypnotics and sedatives, antipyretics, analgesics and anti-inflammatory agents, adrenal hormone preparations, local anesthetics, dermatics for purulence and synthetic antibacterials.

9. The composition according to claim 8, wherein the drug is selected from the compounds consisting of diphenhydramine hydrochloride, chlorpheniramine maleate, clotrimazole, miconazole nitrate, tetryzoline hydrochloride, naphazoline nitrate, ketotifen fumarate, aminophylline, fluorouracil, diazepam, aspirin, indomethacin, sulindac, phenylbutazone, ibuprofen, dexamethasone, triamcinolone, hydrocortisone, lidocaine hydrochloride, sulfisoxazole, kanamycin, tobramycin, erythromycin, norfloxacin and nalidixic acid.

10. The composition according to claim 8, wherein the antihistamines is diphenhydramine hydrochloride, the agent affecting genital organs is miconazole nitrate, the agent for otic and nasal use is tetryzoline hydrochloride, the bronchodilators is aminophylline, the antimetabolic agent is fluorouracil, the hypnotics and sedatives is diazepam, the antipyretics, analgesics and anti-inflammatory agent is indomethacin, the adrenal hormone preparation is dexamethasone, the local anesthetics is lidocaine hydrochloride, the dermatics for purulence is erythromycin and the synthetic antibacterials is norfloxacin.

11. The composition according to claim 1, wherein 2.0% aqueous solution of the methylcellulose has a viscosity of 13 to 12,000 millipascal.sec at 20° C.

12. The composition according to claim 1, wherein the composition shows the gelling temperature of from about 20° C. to about 40° C. and the composition is liquid at the temperature below it.

13. The composition according to claim 1, wherein the composition further comprises at least one of pharmaceutically acceptable buffers, salts, preservative or solubilizing agents.

* * * * *

UNITED STATES PATENT AND TRADEMARK OFFICE
CERTIFICATE OF CORRECTION

PATENT NO. : 5,624,962
DATED : April 29, 1997
INVENTOR(S) : Masanobu TAKEUCHI, et al.

It is certified that error appears in the above-identified patent and that said Letters Patent is hereby corrected as shown below:

In the title page, item [75], line 3, "Miyako Fukushima" should read --Miyako Sasaki--.

Signed and Sealed this

Thirtieth Day of December, 1997

*Attest:*

BRUCE LEHMAN

*Attesting Officer*  *Commissioner of Patents and Trademarks*